US006633383B1

(12) United States Patent
Jackson et al.

(10) Patent No.: US 6,633,383 B1
(45) Date of Patent: Oct. 14, 2003

(54) METHOD AND APPARATUS FOR THE AUTOMATED INSPECTION OF YARN PACKAGES

(75) Inventors: Tobias Jackson, Brooklyn, NY (US); James Knapp, New York, NY (US)

(73) Assignee: Linetech Industries, Inc., Brooklyn, NY (US)

( * ) Notice: Subject to any disclaimer, the term of this patent is extended or adjusted under 35 U.S.C. 154(b) by 14 days.

(21) Appl. No.: 09/696,126

(22) Filed: Oct. 25, 2000

Related U.S. Application Data

(60) Provisional application No. 60/161,011, filed on Oct. 25, 1999.

(51) Int. Cl.[7] ............................. G01N 21/88; G06K 9/00
(52) U.S. Cl. ..................... 356/430; 356/238.2; 382/111
(58) Field of Search ..................... 386/429, 430, 386/238.1, 238.2, 238.3; 382/111, 141

(56) References Cited

U.S. PATENT DOCUMENTS

| | | | | |
|---|---|---|---|---|
| 5,224,172 A | * | 6/1993 | Masai .......................... 348/125 |
| 5,239,184 A | * | 8/1993 | Mancosu et al. ......... 250/559.05 |
| 5,825,501 A | * | 10/1998 | Mee et al. .................... 356/429 |
| 5,936,665 A | * | 8/1999 | Vachtsevanos et al. ..... 348/125 |

* cited by examiner

Primary Examiner—Zandra V. Smith
(74) Attorney, Agent, or Firm—McCormick, Paulding & Huber LLP

(57) ABSTRACT

A filament inspection method for detecting abnormalities in a wound yarn package includes illuminating the yarn package while sensing and recording an image of the illuminated yarn package. The method further includes evaluating the recorded image in accordance with predetermined criteria to determine thereby whether the recorded image indicates the presence of any abnormalities in the yarn package.

23 Claims, 9 Drawing Sheets

Binary conversion

METHOD AND APPARATUS FOR THE AUTOMATED INSPECTION OF YARN PACKAGES

CROSS REFERENCE TO RELATED APPLICATIONS

This application claims the benefit of U.S. Provisional Application No. 60/161,011, filed Oct. 25, 1999.

FIELD OF THE INVENTION

This invention relates in general to a method and apparatus for the automated inspection of yarn packages (a.k.a. bobbins and filament bobbins), and specifically to a method and apparatus for the automated inspection of yarn packages to detect overthrows, broken filaments, and loops.

BACKGROUND OF THE INVENTION

Yarns are typically produced by extruding, drawing, twisting or entangling filaments of the yarn through a series of wheels, chambers, rings, applicators, and godets, and then wound up on a spool, or tube, by a winder. Once the tube is wound with yarn, the resulting package is taken off the winder and made ready for shipment. Currently, packages are inspected for defects and conformity to specifications by human operators and, in some selected cases, automated inspection systems.

One known automated inspection system utilizes laser triangulation for the detection of certain which, while capable of detecting overthrown ends, loops, and broken filaments, suffers in that it lacks repeatability and accuracy, and cannot distinguish between these three defects. Also, due to the high amount of image processing required after the surface profile is produced, inspection speed is prohibitively low.

Another known automated inspection system has been described in U.S. Pat. No. 5,138,151 issued to Inada, et al. on Aug. 11, 1992. As disclosed by Inada, a CCD camera records light which has reflected off of yarn strands as a yarn package is rotated. The recorded image is then processed and any straight line image having a length exceeding a predetermined length is considered to be indicative of a defective yarn strand. As the Inada patent relies on the proper angular alignment of incident light to the yarn package, as well as comparisons between successive reflections of light off of yarn strands, the rate of missed defects and falsely identified defects is unacceptably high.

With the forgoing problems and concerns in minds, it is the general object of the present invention to provide an automated inspection method and apparatus which significantly improves upon the detection capabilities and speed of known systems with respect to overthrows, broken filaments, and loops.

OBJECTS AND SUMMARY OF THE INVENTION

It is an object of the present invention to provide a method and apparatus for the automated inspection of yarn packages.

It is another object of the present invention to provide a method and apparatus for the automated detection of overthrows on yarn packages.

It is another object of the present invention to provide a method and apparatus for illuminating the top and bottom of a yarn package with light and for capturing the images with a light sensor.

It is another object of the present invention to provide an algorithm and image processing method to convert a grey-scale video image to a binary (black and white) image prior to the algorithmic detection of overthrows.

It is another object of the present invention to provide an algorithm and image processing method to detect overthrows from binary images by searching for straight vertical lines of continuous white pixels.

It is another object of the present invention to provide a method for selecting a trapezoidal, box, or combination Region of Interest (ROI) within the overthrow images in order to detect all of the aforementioned variations of overthrows.

It is another object of the present invention to provide a method and apparatus for the automated detection and measurement of broken filaments and loops on yarn packages.

It is another object of the present invention to provide a method and apparatus for illuminating the top, side, and bottom of a yarn package with a rectangular region of light and for capturing these illuminated regions with a light sensor.

It is another object of the present invention to provide an algorithm and image processing method to search for straight vertical white lines extending from the white base lines, where the straight vertical white line is a broken filament.

It is another object of the present invention to provide an algorithm and image processing method to search for black gaps between white pixels, where the top white pixel is a broken filament or loop, and the bottom white pixel, or pixel region, is the white base line.

It is another object of the present invention to provide an algorithm and image processing method to search for enclosed black pixels within the white base region.

It is another object of the present invention to provide a method and apparatus for the representation of overthrows, broken filaments, and loops in a defect image plot similar in style to that of a radar screen.

According to one embodiment of the present invention, a filament inspection method for detecting abnormalities in a wound yarn package includes illuminating the yarn package while sensing and recording an image of the illuminated yarn package. The method further includes evaluating the recorded image in accordance with predetermined criteria to determine thereby whether the recorded image indicates the presence of any abnormalities in the yarn package.

These and other objectives of the present invention, and their preferred embodiments, shall become clear by consideration of the specification, claims and drawings taken as a whole.

BRIEF DESCRIPTION OF THE DRAWINGS

FIG. 7b illustrates the binary conversion of the snapshot greyscale image depicted in FIG. 7a.

DETAILED DESCRIPTION OF THE PREFERRED EMBODIMENTS

Figure 1:
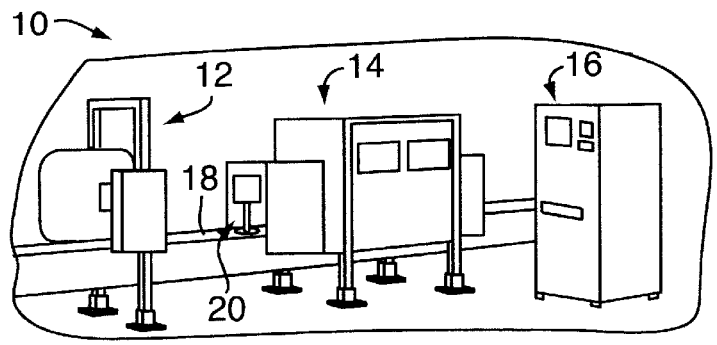
FIG. 1 illustrates a yarn inspection apparatus according to one embodiment of the present invention.

FIG. 1 illustrates a yarn inspection system 10 according to one embodiment of the present invention. As shown in FIG. 1, the yarn inspection system 10 includes a fly station 12, a rotate station 14 and a control station 16. A conveyor belt 18, or the like, provides for movement of wound yarn packages 20 through the fly station 12 and the rotate station 14 under the supervision of the control station 16, as will be described in more detail later.

The fly station 12 is primarily dedicated to a plurality of measurement and detection tasks which require only single frame images to be captured and which are not sensitive to environmental light fluctuations. As such, the fly station 12 is operable to collect these single frame images during active movement of the yarn packages 20 as they pass through the fly station 12. As detailed hereinafter, the fly station 12 may accomplish detection and measurements of certain aspects of each of the yarn packages 20, such as: bulge or ridge detection, transfer tail verification, tube color identification, whiteness or shade identification, package taper measurement, overall package dimension measurement, tube length measurement and package volume measurement (as calculated from 2-dimensional measurements).

The rotate station 14 is located downstream from the fly station 12 and is primarily dedicated to measurement and detection tasks which require multiple images to be captured while the yarn packages 20 rotate and/or which require isolation from environmental light changes. It is thus imperative that the passage of the yarn packages 20 through the rotate station 14 be momentarily halted to acquire these images. As detailed hereinafter, the rotate station 14 may accomplish detection and measurements of certain aspects of each of the yarn packages 20, such as: dirt, grease and stains, damaged tubes and yarn overthrows, loops and broken filaments.

Figure 3:
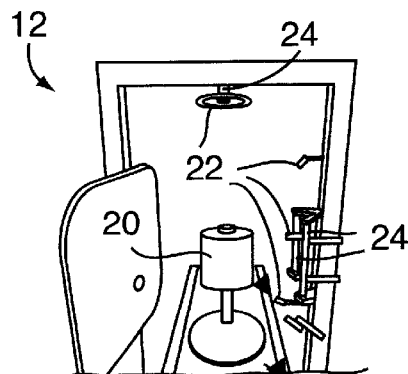
FIG. 3 illustrates a fly station of the yarn inspection apparatus shown in FIG. 1.
Figure 4:
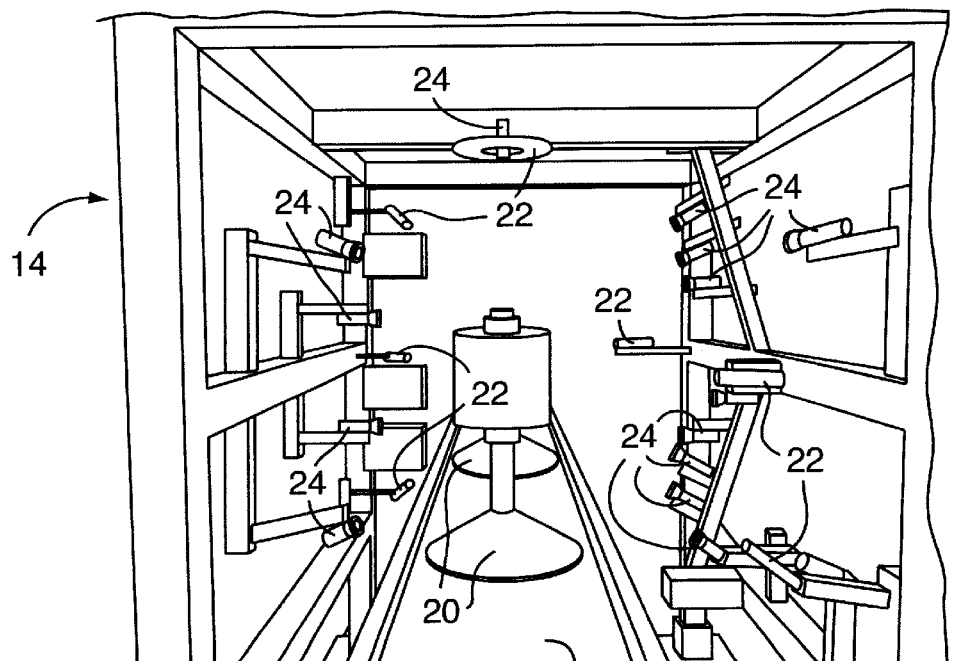
FIG. 4 illustrates a rotate station of the yarn inspection apparatus shown in FIG. 1.

As illustrated in FIGS. 3 and 4, both the fly and rotate stations, 12 and 14 respectively, contain a plurality of separate lighting modules, or lights, 22 and light sensing modules, or sensors, 24. As discussed hereinafter, the lights or lighting modules 22 may be any type of illumination technique, including but not limited to diffuse white light, structured white light, monochromatic light, coherent light, collimated light, LED light, laser light, etc., while the light sensing modules 24 include CCD cameras and the like.

It will be readily appreciated that the structured lighting techniques described hereinafter are lighting techniques that serve to emphasize the optical properties of the defects themselves, which in turn makes image processing of the resultant image data much simpler than extracting the features from a complex surface profile map. By allowing the simplification of image processing, the overall inspection task becomes faster, more accurate, more repeatable, and allows quantification and differentiation of the three main defects mentioned previously. It will also be readily appreciated that alternative configurations of the lights 22 and the light sensing modules 24 may also be employed without departing from the broader aspects of the present invention, provided that these alternative configurations provide the required illuminated views of the yarn packages 20.

Figure 2:
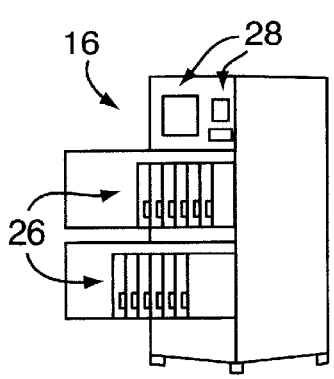
FIG. 2 illustrates a control station of the yarn inspection apparatus shown in FIG. 1.

The control station 16 shown in FIG. 2 is comprised of a plurality of computers 26 which are capable of receiving, generating and storing machine readable data. The control station 16 further houses information and video displays and monitors 28 and other commonly known control hardware to allow a user to actively, or passively through a previously entered computer program, coordinate and control the fly station 12, the rotate station 14, the lights 22, the light sensing modules 24 and the conveyor belt 18. The control station 16 utilizes a set of computer algorithms, to be described in more detail later, to measure and detect defects in the yarn packages 20.

Figure 5A:
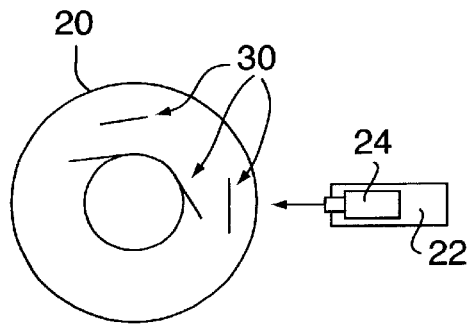
FIG. 5a illustrates a top view of the illumination and image acquisition of a yarn package, according to one embodiment of the present invention.

The method and apparatus utilized for the automated detection of overthrows in the yarn packages 20 will now be described. As defined hereinafter, 'overthrows' 30 comprise portions of the wound yarn which are exhibited by straight strands of yarn that lie flat across the top or bottom of the yarn package 20, and are perpendicularly bisected, typically at their midpoint, by the radius of the yarn package 20, as shown in FIG. 5a. The overthrows 30 are commonly the result of a throwing mechanism overthrowing the yarn past the edge of yarn bunch while the yarn winds on a horizontal axis. While the detection of overthrows 30 are mentioned herein, the present invention is equally applicable to overthrows 30, matted overthrows, wrap-arounds (an overthrow which is wrapped-around the yarn tube 32) and any other name given to such defects.

Figure 5B:
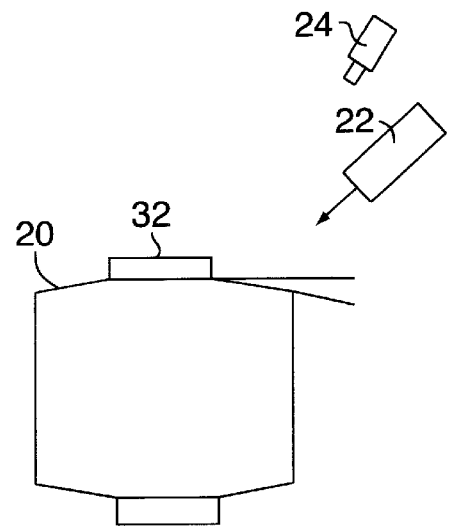
FIG. 5b illustrates a side view of the illumination and image acquisition of a yarn package, according to one embodiment of the present invention.

In order to begin the detection of overthrows 30, the yarn package 20 is momentarily halted and then rotated within the rotate station 14, as depicted in FIG. 4. As shown in the side view of FIG. 5b, the lights 22 are positioned to provide angled illumination of the top or bottom of the yarn package 20, wherein the angle of incidence of the emitted light is between approximately 45° to approximately 90° to the surface of the yarn and directed from the outside of the yarn package 20 toward the center of the yarn package 20 following a trajectory in line with the radius of the yarn package 20. The relationship between the package taper angle ø and the direction of the light emanating from the lights 22 simply needs to be sufficient in order to create a shadow line whenever an overthrow becomes perpendicular to the direction of the light. In addition, the position of the light sensing modules, or sensor 24, is fixed so that shadow contrast is optimized and emphasized on the light sensor 24. One possible geometric positioning of the light 22, the sensor 24, and the yam package 20 is illustrated in FIGS. 5a and 5b.

Recent experiments have proven that the following light types are feasible for producing sufficiently contrasting shadows: diffuse light, expanded laser light, and projected light. These lighting techniques can be further optimized using colored lighting: one color for diffuse filling light (blue light, for instance) from a high angle and another color (red light, for instance) preferably lo used at a lower angle to the yarn surface. This improves contrast so that the shadow lines are more easily detected.

Figure 6:
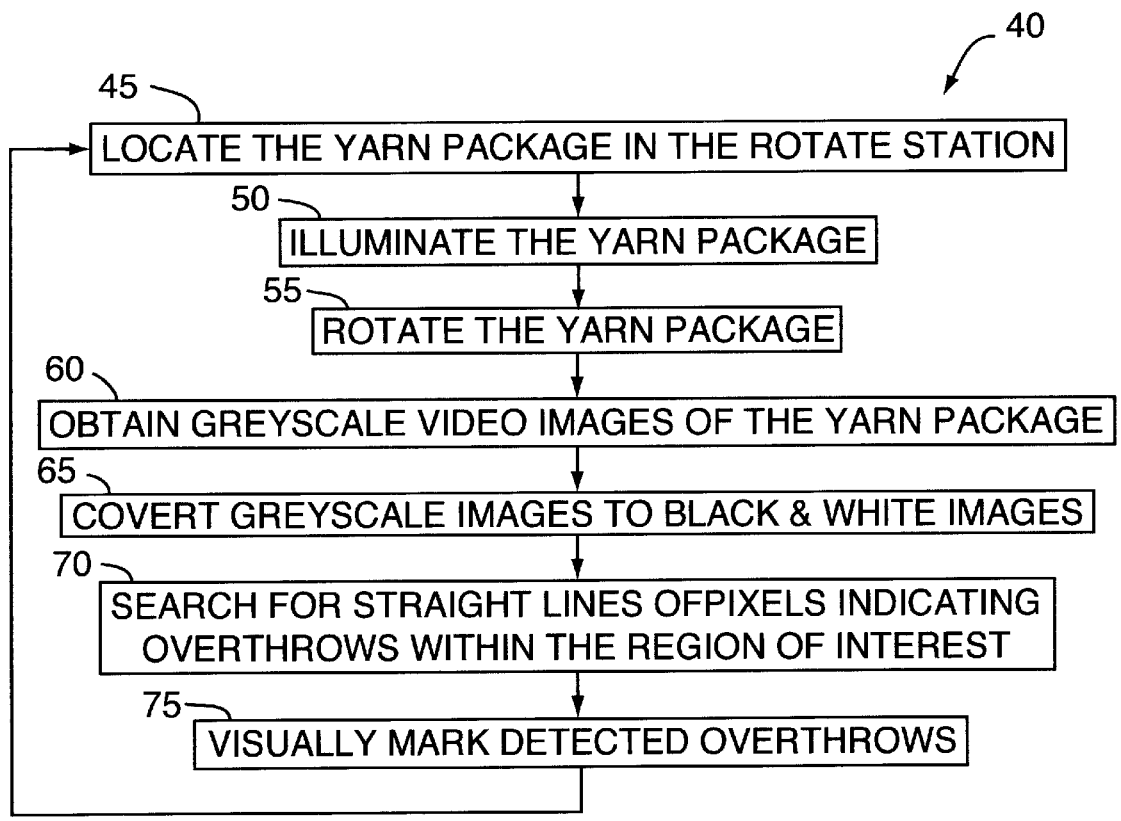
FIG. 6 is a flow diagram of an inspection algorithm for the detection of overthrows, according to one embodiment of the present invention.

FIG. 6 is a basic flow diagram of a computer inspection algorithm 40 employed by the control station 16 to detect overthrows. As discussed above, step 45 of the algorithm 40 causes the yarn package 20 to be halted within the rotate station 16. Step 50 initiates illumination of the yarn package 20 by the lights 22 wherein the incident light from the lights 22 is directed towards the surface of the yarn package 20 at an angle preferably between 45° and 90°. The yarn package 20 is then caused to rotate within the rotate station 16 to enable the sensors 24 to view and record the resultant images as a plurality of greyscale snapshot images, as indicated in step 60. It will be readily apparent that the rotation of the yarn package 20 may be accomplished in any known conventional manner wherein the speed of rotation is variable and largely dependent upon the specific technical capabilities of the component equipment utilized in the yarn inspection system 10 of the present invention.

Returning to FIG. 6, step 65 indicates the conversion and storage of the greyscale images obtained in step 60 to binary, or black and white, video images comprised of a two-dimensional pixel array. Overthrows themselves are determined in step 70 by evaluating the pixels of the binary snapshot images to discover if straight line pixel segments having either a uniform black or white coloration exist and, if so, if they exhibit a predetermined orientation, as will be described in more detail later. In the preferred embodiment of the present invention, the control station 16 is preferably set to identify straight line yarn segments as a string of uniform white pixels. When identified, therefore, the straight line uniform segment of white pixels are visually highlighted or marked as an overthrow 30 on the information and video monitors 28 (shown in FIG. 9). As will be appreciated, information corresponding to the location and number of overthrows for an individual yarn package may be stored by the control station 16 for subsequent use. This algorithm is repeatedly accomplished for each of the yarn packages 20 until all overthrows have been detected.

It is therefore an important aspect of the present invention that the inspection algorithm 40 converts the detected snapshot greyscale images to black and white images in order to nullify differences in color and reflectivity between sections of the yarn package 20. In this manner, the straight line pixel segments of uniform coloration may be more easily delineated by the control station 16, thereby reducing the detection of false overthrows while ensuring detection of all true overthrows.

Figure 7A:
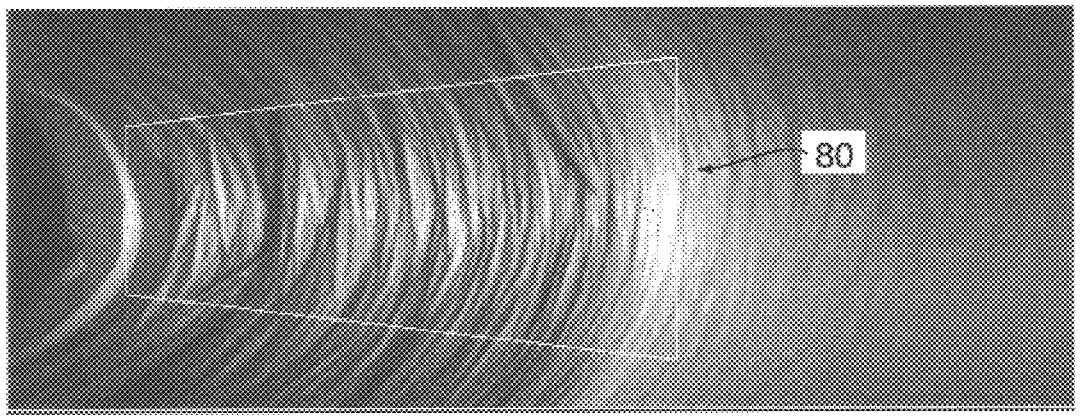
FIG. 7a illustrates a snapshot greyscale image of a yarn package prior to binary conversion.
Figure 7B:
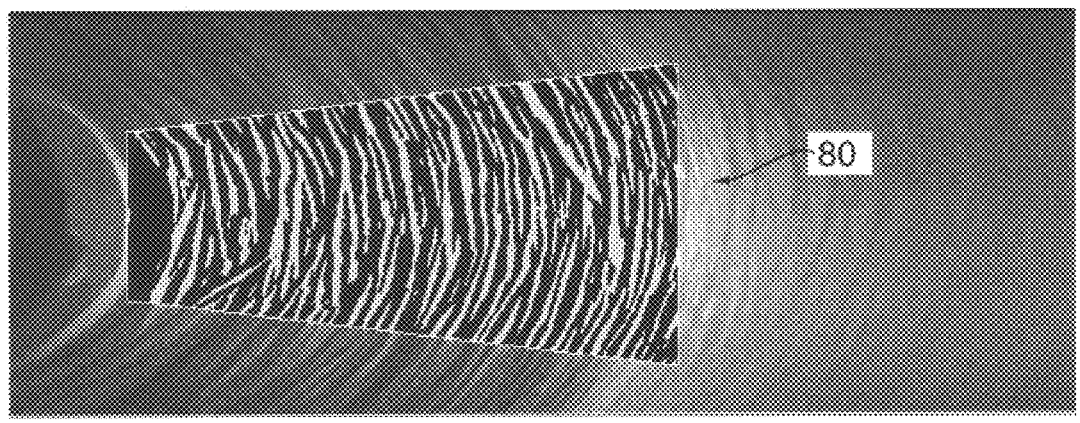
Figure 8A:
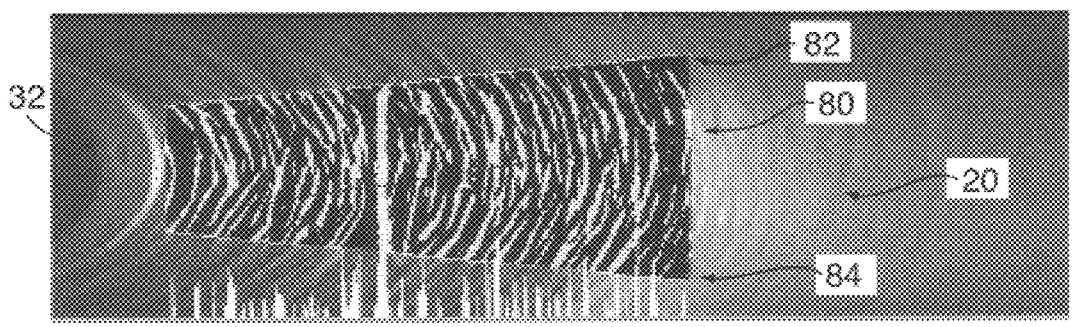
FIG. 8a illustrates a binarized trapezoidal region of interest as defined in a greyscale image recorded by the yarn inspection system of the present invention.
Figure 8B:
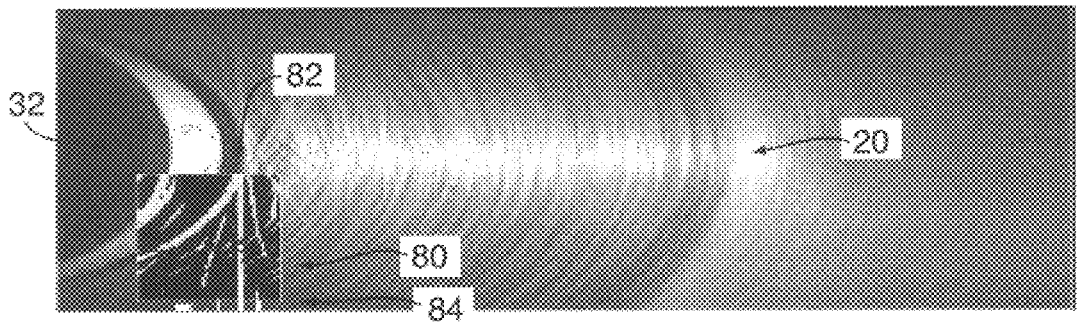
FIG. 8b illustrates a binarized square region of interest as defined in a greyscale image recorded by the yarn inspection system of the present invention.
Figure 8C:
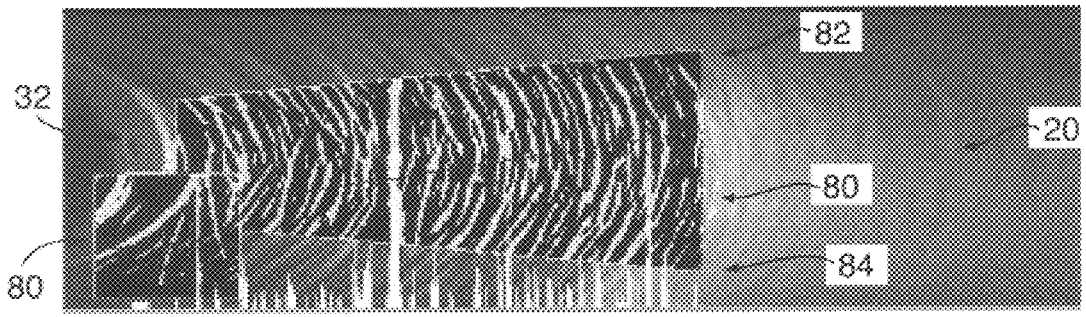
FIG. 8c illustrates a binarized combination region of interest as defined in a greyscale image recorded by the yarn inspection system of the present invention.

FIGS. 7a and 7b illustrate the conversion of a single greyscale snapshot, shown in FIG. 7a, to a binary or black and white image, shown in FIG. 7b. As further indicated in FIGS. 7a and 7b, the entirety of the greyscale image of FIG. 7a is not converted to the binary image seen in FIG. 7b, rather only that portion within a user-defined region of interest (hereinafter ROI) 80 is so converted. By allowing users to define differing ROIs 80, the yarn inspection system 10 of the present invention permits one or more specific regions of the yarn package 20 to be inspected pursuant to the particular concerns of a given user. As best seen in FIGS. 8a–8c, a user may define trapezoidal or box shaped ROIs 80, or a combination thereof, within the snapshot images.

It is therefore another important aspect of the present invention to provide this variable ROI 80 as part of the inspection algorithm 40, wherein the height of the ROI 80 is equal to the user-defined maximum acceptable overthrow length or proportion thereof. Such concerns are important as a yarn producer may want to provide shorter overthrow length acceptability standards to overthrows which appear near the tube 32 and provide longer overthrow length acceptability standards to overthrows which appear near the outer diameter of the yarn package 20. (This is due to the fact that overthrows which appear near the tube have a greater possibility of snagging during unwinding compared to overthrows of equal length which appear near the outer diameter of the package.) Therefore, the yarn inspection system 10 of the present invention allows a user to define the trapezoidal ROI 80 of FIG. 8a, where vertically continuous white pixels must stretch a longer distance (from the upper ROI line 82 to the lower ROI line 84) in the outer diameter region of the package than vertically continuous white pixels near the tube 32 in order to be detected as an overthrow, as will be described in more detail shortly.

Moreover, while the basic inspection algorithm 40 utilizing a rectangular or trapezoidal ROI 80 is sufficient to detect standard overthrows, it may not be sufficient to detect wrap-arounds in certain cases because wrap-around segments appear as a section of an overthrow having an endpoint at the intersection of the tube 32, as shown in FIG. 8b, and therefore will only be considered as short lengths of vertically continuous white pixels if only the rectangular or trapezoidal ROI 80 is employed. Therefore, as depicted in FIG. 8b, a user may want to provide a box ROI 80 near the tube having an upper ROI line 82 aligned with the radius of the yarn package 20 and having a lower ROI line 84 placed below at a distance equal to the maximum acceptable wrap-around segment length. Further, the present invention provides a combination trapezoidal and box ROIs 80, as discussed previously and shown in FIG. 8c, to detect all variations of overthrows simultaneously.

As discussed previously, the conversion of snapshot images in step 65 of the inspection algorithm 40 from a greyscale representation to a binary representation is accomplished utilizing a system of pixel differentiation. As originally recorded by the sensors 24, the snapshot images of the yarn package 20 are each comprised of a two-dimensional pixel array having a gradient associated therewith ranging from bright lines, which typically represent the yarn material, to dark lines or areas, which typically represent the shadows cast by the yarn material. It is vitally important that the binary representations of the greyscale images properly delineate between these light and dark areas to provide for accurate detection of individual yarn threads and, therefore, overthrows.

In order to accomplish this pixel differentiation, step 65 of the inspection algorithm 40 begins by designating a pixel within the ROI chosen for a given yarn package 20 as an 'object pixel'. The inspection algorithm 40 then converts this object pixel to a black or white pixel by computing, first, the greyscale value(s) of a pixel or a predetermined number of pixels to the left of the object pixel and the greyscale value(s) of a pixel or a predetermined number of pixels to the right of the object pixel. The summation of the greyscale values to the left and right of the object pixel are then compared to one another to determine the numerical difference therebetween. If this numerical difference is below an established threshold value, the object pixel will be converted to 'black', while if the numerical difference is at or above the threshold value the object pixel will be converted to 'white', thus producing a binary or black and white image. The threshold value may alternatively be inputted by a user, may be a stored value corresponding to the specific lights 22 utilized and yarn material being inspected, or may instead be calculated in real-time from a median greyscale value of the ROI.

It will be readily apparent that by utilizing the above process the inspection algorithm 40 may assuredly distinguish between individual yarn threads and their shadows, provided that no extraneous light is allowed to enter the rotate station 16 during the inspection process. Towards this end, the rotate station 16 should be equipped with an enclosure or the like for light shielding during the inspection process.

An important aspect of the present invention resides in quantifying the predetermined number of pixels to be analyzed on either side of the object pixel, as discussed above. Given that pixel differentiation and the subsequent binary conversion is utilized to map the physical delineation between individual strands of yarn in the yarn package 20, the present invention contemplates utilizing a ratio between the cross-sectional area of the yarn strands to be inspected and the number of pixels on either side of the object pixel to be analyzed. That is, the larger the cross-sectional area of the yarn wound on the yarn package 20, the greater the number of pixels on either side of the object pixel that must be analyzed. For very small diameter yarns, only a pixel or two may be required to be analyzed on either side of the object pixel in order to distinguish specific yarn strands for the purposes of binary mapping, while larger diameter yarns will require a correspondingly greater number of pixels on either side of the object pixel to accomplish the same goal. It will be readily appreciated, therefore, that the number of pixels to be analyzed on either side of the object pixel may be inputted by a user, may be a stored value in accordance with a known yarn type or calculated in real-time during initial inspection of the yarn package 20.

It should be noted that the light sensors 24 which record images of the rotating yarn package 20 are capable of recording a variable number of shapshot images with each rotation of the yarn package 20. In the preferred embodiment of the present invention, a snapshot image is acquired approximately every 1 degree of rotation of the yarn package 20. A subsequent determination as to the presence of an overthrow is then made independently on the basis of, and with respect to, each of these images.

It is therefore another important aspect of the present invention that, as opposed to prior art devices and methods, the determination of overthrows occurs without comparing subsequent recorded views to previous recorded views. In this manner, the present invention not only limits complex processing time and reduces the complexity of both the equipment and computer software needed, but increases the reliability of detecting overthrows as any error in overthrow detection for a given image does not carry over to the evaluation of the next image. As will be appreciated, by isolating the evaluation of each image from all others, the contaminating effects of errors in overthrow detection may be effectively eliminated. Moreover, by varying the number of images acquired per rotation of the yarn package 20, the present invention ensures that sufficiently small ROIs may be selected to overlap one another. Therefore, even if a detection error occurs in a given image, each individual overthrow may be accurately detected by evaluation of preceding or subsequent images.

Figure 9:
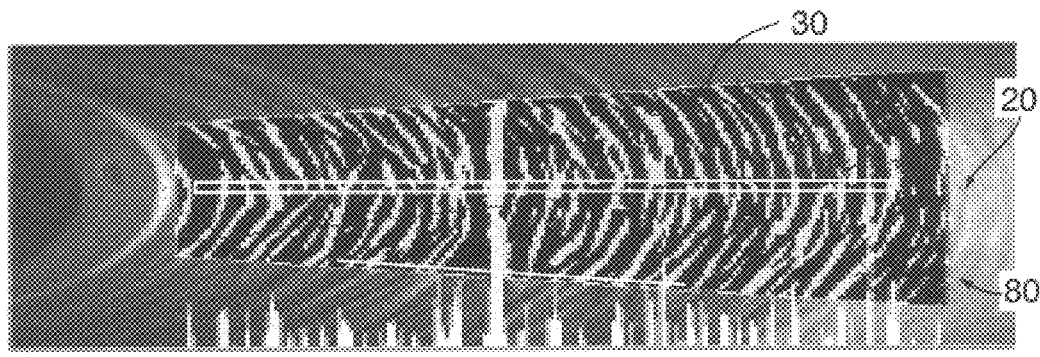
FIG. 9 illustrates an identified and marked overthrow in a greyscale image recorded by the yarn inspection system of the present invention.

As indicated previously, the nature of an overthrow abnormality mandates that each overthrow will be exhibited as a straight line substantially perpendicular to a radial line of the yarn package. The present invention directly utilizes this comparative architecture to assist in the accurate determination of overthrows in a manner heretofore unknown in the art. In the preferred embodiment of the present invention, the user-defined ROI 80 is controlled to be centered about a radial line of the yarn package 20, wherein the inspection algorithm 40 only identifies as overthrows those straight line segments of pixels which are substantially perpendicular to the radial line. In practice, these detected overthrows 30 appear as vertical straight lines of pixels extending from an upper boundary of the ROI 80 to a lower boundary of the ROI 80, as shown in FIG. 9. It will be readily appreciated that alternative detection techniques may be utilized which do not require that the ROI 80 be centered about a radial line of the yarn package 20, provided that the angular orientation of the ROI 80 is taken into account when the inspection algorithm 40 determines if any straight line of pixels occurring in the ROI 80 is substantially perpendicular to a radial line of the yarn package 20.

The present invention preferably limits identification of overthrows to those substantially perpendicular straight line pixel segments which extend from an upper boundary of the ROI 80 to a lower boundary of the ROI 80 in order to protect against false identification of overthrows. This false identification may occur if the ROI 80 is chosen to be so small in area that properly wound yarn strands would appear as straight lines extending part way through the ROI 80.

In operation, the yarn inspection system 10 identifies overthrows in a yarn package 20 by illuminating the yarn package 20 and taking a plurality of snapshot images as the yarn package 20 is rotated. Each of these resultant images are electronically processed to discover straight line pixel segments, wherein overthrows are identified if any of the straight line pixel segments are determined to be substantially perpendicular to a radial line of the yarn package 20. Pixel differentiation, binary conversion of the recorded images, orientation of the ROI 80 about a radial line of the yarn package 20 and sensing if a straight line pixel segment extends from a top ROI 80 boundary to a bottom ROI 80 boundary are all techniques which improve speed and detection capabilities while reducing false identifications and equipment complexity.

Figure 10:
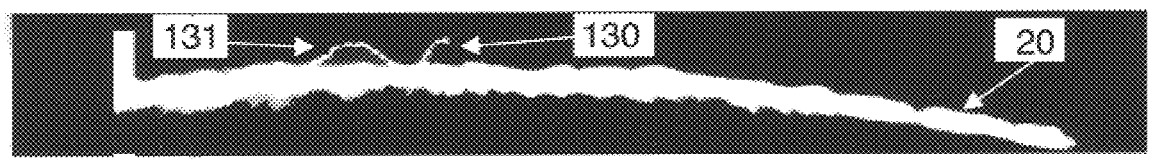
FIG. 10 illustrates two abnormalities present in a given yarn package, a broken filament and a loop.

The method and apparatus utilized for the automated detection of broken filaments and loops in the yarn packages 20 will now be described. As defined hereinafter, 'broken filaments' 130 comprise filaments of yarn that exit the surface of the yarn package 20, as depicted in FIG. 10. While the detection of broken filaments 130 are mentioned herein, the present invention is equally applicable to broken filaments 130, snags (groupings of multiple broken filaments in a given area on the package 20 surface) and any other name given to such defects. As defined hereinafter, 'loops' 131 comprise filaments of yarn that exit and enter the bunch in an arch-like path, as depicted in FIG. 10. While the detection of loops 131 are mentioned herein, the present invention is equally applicable to any other name given to such defects.

Figure 11A:
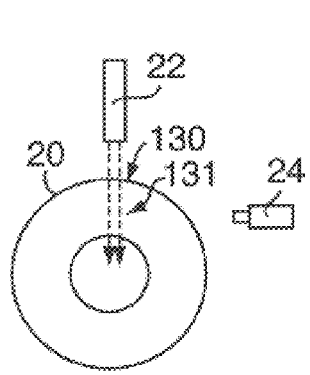
FIG. 11a is a top view of the illumination and image acquisition of broken filaments and loops.
Figure 11B:
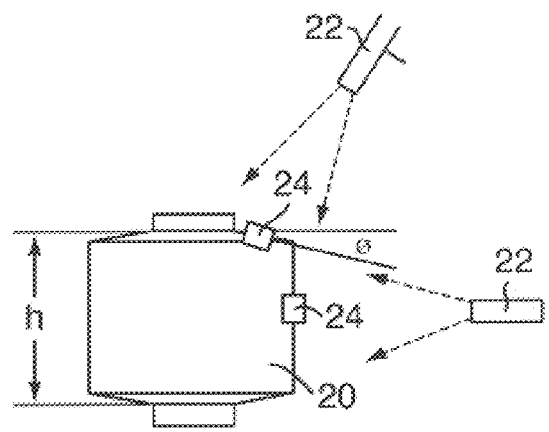
FIG. 11b is a side view of the illumination and image acquisition of broken filaments and loops.

In order to begin the detection of broken filaments 130 and loops 131, the yarn package 20 is momentarily halted and then rotated within the rotate station 14, as depicted in FIG. 4. One possible geometric positioning of the light 22, the sensor 24, and the yarn package 20 is illustrated in FIGS. 11a and 11b. As shown in the top view of FIG. 11a and the side view of FIG. 11b, the lights 22 are positioned to provide a column of illumination onto the top, bottom, or side of the yarn package 20, wherein the angle of incidence of the emitted light is approximately perpendicular to the surface of the yarn and the column of illumination is directed from the outside of the yarn package 20 following a trajectory in line with the radius of the yarn package 20. In addition, the position of the light sensing modules, or sensor, 24 is fixed so that, given the package height h and package taper angle ø, the sensor 24 is approximately level with the horizon of the package 20 and rotated along the line-of-sight axis by an angle equal to ø so that the horizon of the package 20 is horizontal to the sensor 24. It will be readily apparent that the positioning and rotation of the sensor 24 may be accomplished in any known conventional manner wherein the speed and resolution is variable and largely dependent upon the specific technical capabilities of the component equipment utilized in the yarn inspection system 10 of the present invention.

Figure 12:
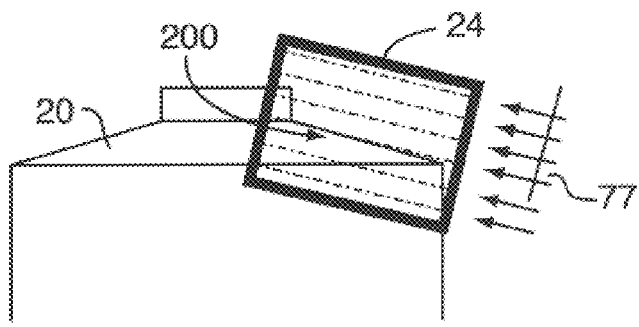
FIG. 12 illustrates an orientation of the image acquisition sensor with respect to the yarn package being investigated, according to one embodiment of the present invention.

An important aspect of the present invention is to rotate the sensor 24 by an angle equal to the package taper angle ø as described above. The rotation of the sensor 24 serves to enhance the computer detection algorithm by lining up the horizon of the yarn package 20 with the horizontal rows of pixels 77 as recorded by the sensor 24, as depicted in FIG. 12.

Figure 13A:
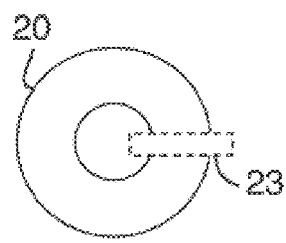
FIG. 13a is a top view of the orientation of a rectangular inspection light.
Figure 13B:
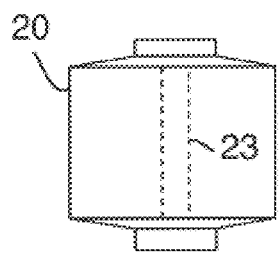
FIG. 13b is a side view of the orientation of a rectangular inspection light.
Figure 14:
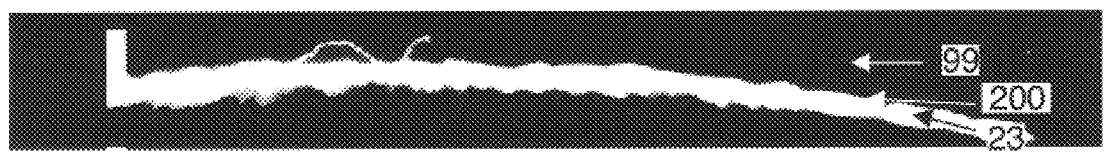
FIG. 14 illustrates the contrast between an recorded image and the background.

An important aspect of the present invention is the type of light 22 used to illuminate the top, bottom, or side of the yarn package 20. It is necessary to create a rectangular region of light 23 which is bright and which has sharply defined edges, as depicted in FIGS. 13a and 13b. The rectangular region of light 23 needs to be bright to ensure that substantial light is reflected off all broken filaments 130 and loops 131 in order to be detected by the sensor 24. The rectangular region of light 23 needs to have sharply defined edges so that images captured by the sensor 24 have sharp contrast along the horizon 200, said horizon 200 being the line existing between the rectangular region of light 23 and the background 99, as depicted in FIG. 14. Sharp contrast along the horizon 200 is necessary because, if sharp contrast exists along the horizon 200, then sharp contrast will also necessarily exist between any broken filaments 130 and the background 99, and between any loops 131 and the background 99. And further, sharp contrast between broken filaments 130 and the background 99 and between loops 131 and the background 99 are necessary so that computer conversion from a greyscale image to a binary, or black and white, image is accurate and repeatable.

Recent experiments have proven that both masked collimated and coherent light types are feasible for producing sufficiently bright rectangular regions of light 23 with sharply defined edges on the top, bottom and side surfaces of the yarn package 20. Monochrome, infrared, visible, and ultraviolet light can all be used for this purpose.

Figure 15:
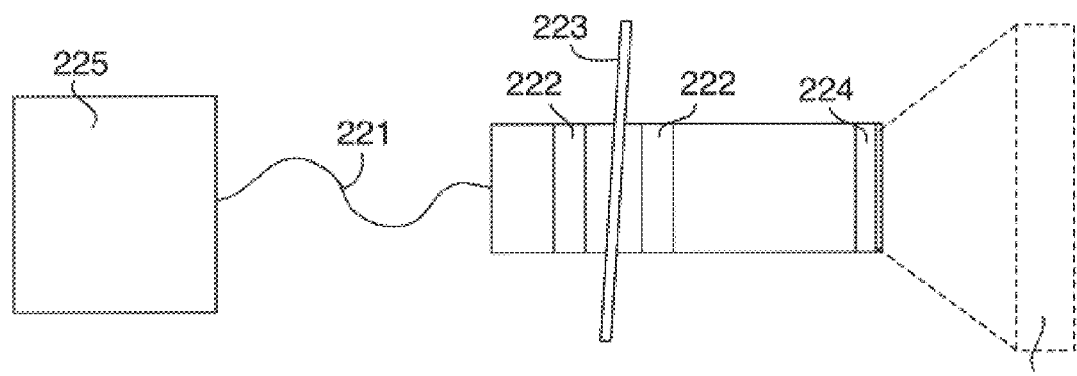
FIG. 15 illustrates an inspection light generating device, according to one embodiment of the present invention.

FIG. 15 is one type of light 22 that can be used to illuminate a bright rectangular region of light 23 on the top, bottom, and side surfaces of the yarn package 20. The light 22 is comprised of a light source 225, a fiber optic light guide 221, two cylindrical lenses 222, a mask 223, and an imaging lens 224 to create a bright, rectangular region of light 23. Light is supplied to the fiber optic light guide 221 by a light source 225. The light source 225 can be either a light bulb, an LED array, or other light source. Photons are carried from the source 225 through the fiber optic light guide 221 to two in-line cylindrical lenses 222 which collimate the light into a rectangle. A rectangular mask 223 is inserted in between the two cylindrical lenses in order to give the four edges of the collimated light a clean, sharp edge. After exiting the second cylindrical lens 222, the light is imaged by a standard imaging lens 224 onto the surface of the yarn package 20. The focal lengths of all three lenses 222 & 224 and the size of the mask 223 can be varied to vary the projected light size and fluence. The intensely bright rectangular region of light 23 that results from the light type as depicted in FIG. 15 helps the sensor 24 acquire images of broken filaments 130 and loops 131 with excellent contrast.

Figure 16:
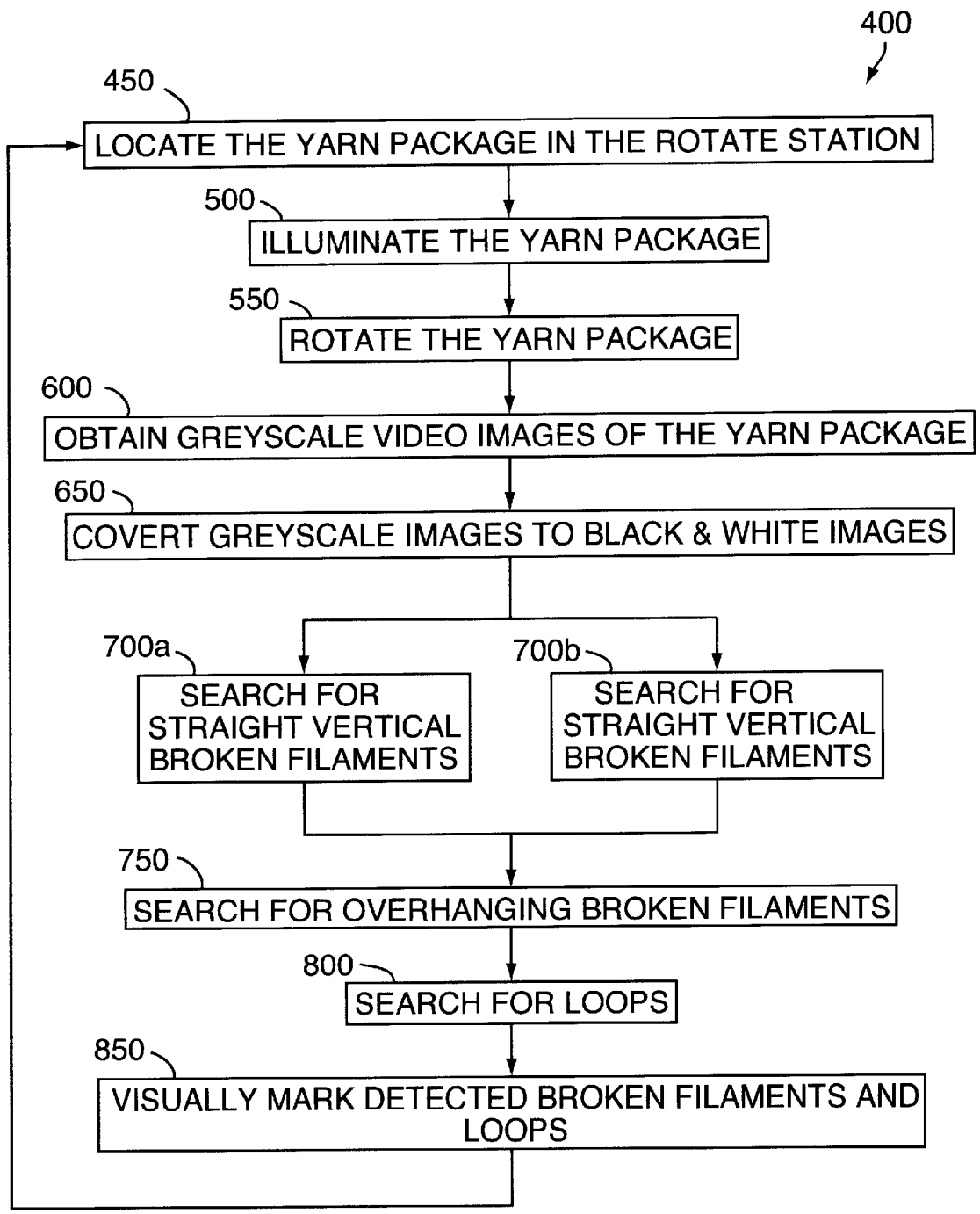
FIG. 16 is a flow diagram of an inspection algorithm for the detection of broken filaments and loops, according to one embodiment of the present invention.

FIG. 16 is a basic flow diagram of a computer inspection algorithm 400 employed by the control station 16 to detect broken filaments 130 and loops 131 from the acquired video images of the yarn package 20. As discussed above, step 450 of the algorithm 400 causes the yarn package 20 to be halted within the rotate station 16. Step 500 initiates illumination of the yarn package 20 by the lights 22 to create the bright rectangular region of light 23 on the surface of the yarn package 20. The yarn package 20 is then caused to rotate within the rotate station 16 to enable the sensors 24 to view and record the resultant images as a plurality of greyscale snapshot images of the yarn package 20, as indicated in step 600. It will be readily apparent that the rotation of the yarn package 20 may be accomplished in any known conventional manner wherein the speed of rotation is variable and largely dependent upon the specific technical capabilities of the component equipment utilized in the yarn inspection system 10 of the present invention.

Figure 17:
FIG. 17 illustrates an example of detected straight and overhanging broken filaments.
Figure 18:
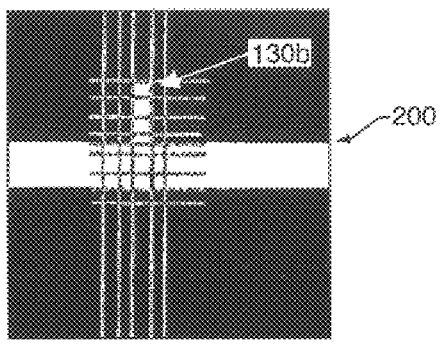
FIG. 18 illustrates the pixel mapping and detection of straight broken filaments, according to a first inspection algorithm.
Figure 19:
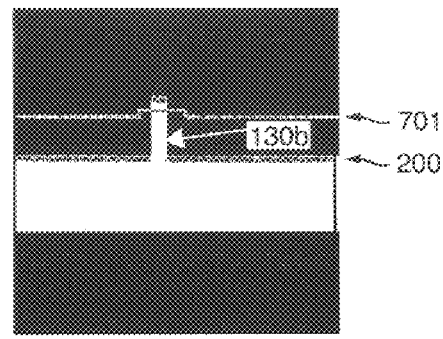
FIG. 19 illustrates the pixel mapping and detection of straight broken filaments, according to a second inspection algorithm.

Returning to FIG. 16, step 650 indicates the conversion and storage of the greyscale images obtained in step 600 to binary, or black and white, video images comprised of a two-dimensional pixel array. Straight vertical broken filaments 130a themselves are determined in step 700a or 700b using either computer detection algorithm 700a or 700b. Straight vertical broken filaments 130a are defined as broken filaments which extend up from the horizon along a pixel column, or along multiple columns if the broken filament 130a is thicker than one pixel column, without bending into the pixel columns to the right or to the left, as depicted in FIGS. 17,18 & 19. Algorithm 700a evaluates the pixels of the binary snapshot images to discover if straight pixel segments which extend vertically from the horizon 200 exist, as depicted in FIG. 18. Algorithm 700a operates by searching downward through each pixel column for white pixels. Once a white pixel in a given pixel column is identified, the algorithm 700a determines the color (black or white) of a predetermined number of neighboring pixels to the left and to the right. If the neighboring pixels to both the left and right are black, the identified pixel is determined to be a straight vertical broken filament 130a, or portion thereof. If a predetermined number of neighboring pixels to the left and right are not both black, the identified pixel is determined to be part of the horizon 200, and determined not to be a portion of a broken filament 130a. It should be mentioned that the number of predetermined pixels investigated on either side of the identified pixel is in direct proportion to the thickness of the yarn filaments that exist on the yarn package 20, and is therefore variable in accordance with user-defined parameters or automatically under the direction of the control station 16.

Algorithm 700b also evaluates the pixels of the binary snapshot images to discover if straight pixel segments which extend vertically from the horizon 200 exist, as depicted in FIG. 19. Algorithm 700b operates by identifying all the white pixels that comprise the horizon 200. Then algorithm 700b smoothes the horizon 200 into a smoothed horizon 701, where the vertical height of each pixel contained on the smoothed horizon 701 is determined by calculating the average vertical height value of a predetermined number of consecutive pixels existing on the horizon 200. Algorithm 700b determines any pixel on the horizon 200 to be a straight vertical broken filament 130a if the vertical height of the pixel on the horizon 200 exceeds the vertical height of the pixel on the smoothed horizon 701 by a predetermined value which corresponds to a predetermined detection sensitivity value.

Figure 20:
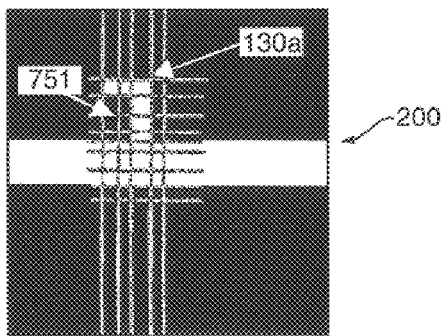
FIG. 20 illustrates the pixel mapping and detection of overhanging broken filaments.

It is therefore another important aspect of the present invention that determination of broken filaments or loops is not accomplished until the artificially smooth horizon 701 is generated by the inspection algorithm 400, thereby reducing the occurrence of false detection of these abnormalities. Returning to FIG. 16, overhanging broken filaments 130b themselves are determined in step 750 by another computer detection algorithm. Overhanging broken filaments 130b are exhibited by broken filaments which extend up from the horizon 200 and then turn to the left and/or to the right, creating an overhang of white pixels above a small area of the black pixels 751, said small area being a portion of the background 99, as depicted in FIG. 17. The algorithm 750 evaluates the pixels 751 of the binary snapshot images to discover if overhanging broken filaments 130b which extend vertically from the horizon 200 exist, as depicted in FIG. 20. Algorithm 750 operates by searching downward through each pixel column of a binary image for white pixels. Once a white pixel is identified in an evaluated pixel column, the algorithm 750 continues to search downward through the pixel column in which the white pixel was discovered. If the color of the evaluated pixels change from white to black, only once, and if the algorithm 400 determines that the evaluated pixel 30 column has reached the bottom of the binary image, then the algorithm 750 determines that no overhanging broken filaments 130b exist within that pixel column. If, on the other hand, the algorithm 750 searches downward through the pixel column after detection of a white pixel and finds that the color of the evaluated pixels change from white to black and then to white again and back to black, wherein the algorithm 400 determines that the evaluated pixel column has reached the bottom of the binary image, then the algorithm 750 determines that an overhanging broken filament 130b exists within that pixel column.

It will be readily appreciated that although the algorithm 400 has been described as searching for a particular arrangement of colored pixels, column by column in a binary image beginning at the top of the binary image and working downwards to the bottom of the binary image, the present invention is not limited in this regard. Alternative searching methodologies may be employed, such as searching each column from the bottom of the binary image and working 'up', provided that the overhanging broken filaments are detected utilizing the color differentiation between black and white pixels in any single pixel column.

Figure 21:
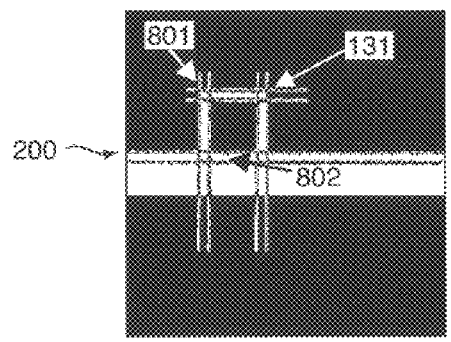
FIG. 21 illustrates the pixel mapping and detection of filament loops filaments.

Returning to FIG. 16, loops 131 themselves are determined in step 800 by another computer detection algorithm. The algorithm 800 evaluates the pixels of the binary snapshot images to discover if loops 131 which extend vertically from the horizon 200 exist, as depicted in FIG. 21. The algorithm 800 operates by searching from left to right along the white pathway of pixels which identify the horizon 200. If the horizon 200 splits into an upper white pixel pathway 801 and a lower white pixel pathway 802 and then rejoin at any number of pixels to the right, then algorithm 800 determines that a loop exists and is defined by the splitting pathways, 801 and 802 respectively.

When identified, broken filaments 130a and 130b, as well as loops 131, are visually highlighted or marked on the information and video monitors 28. As will be appreciated, information corresponding to the location and number of broken filaments and loops for an individual yarn package may be stored by the control station 16 for subsequent use. This algorithm is repeatedly accomplished for each of the yarn packages 20 until all broken filaments and loops are detected.

Figure 22:
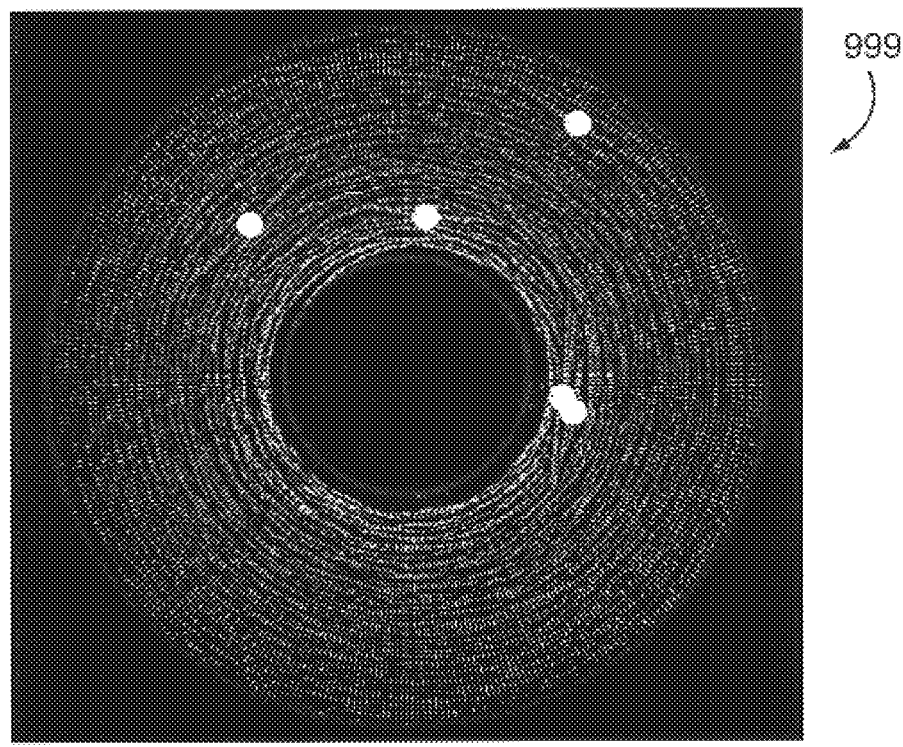
FIG. 22 illustrates the mapping of detected overthrow locations on a yarn package.

The present invention also contemplates compiling a map 999, table, or the like of the visual highlight, or marks, of overthrows 30, broken filaments 130, and loops 131 in order to identify, locate and count the number of these abnormalities on the yarn package 20. As discussed previously, while the yarn package 20 rotates, the camera acquires images of overthrows 30, broken filaments 130 and loops 131. For each image, a single horizontal pixel line is copied and is plotted as a single centerline within a resultant circular map 999 which represents the circular yarn package 20 from a top or bottom view. For overthrow images, the single horizontal pixel line is preferably copied from the horizontal center line of the ROI 80 in binary color depth. As illustrated in FIG. 22, a visual indicator is overwritten on the map 999 to identify the approximate midpoint of each of the detected overthrows 30.

Figure 23:
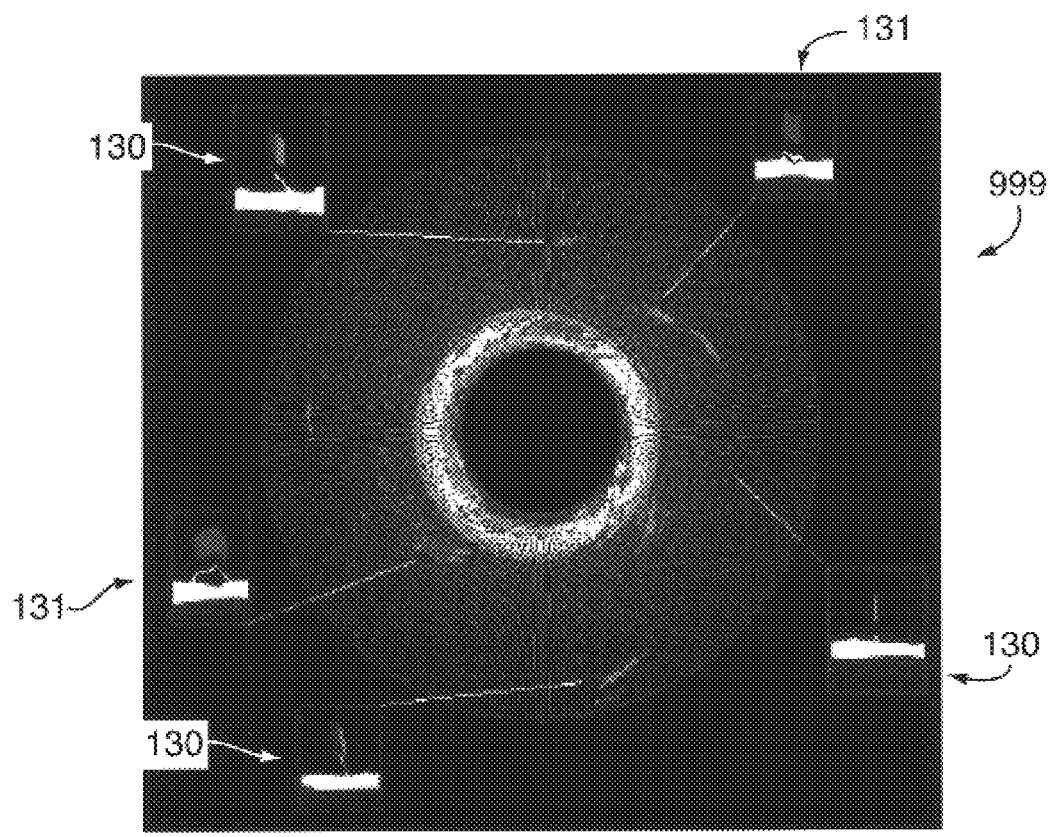
FIG. 23 illustrates the mapping of detected broken filament and loop locations on a yarn package.

For broken filament and loop images, the single horizontal pixel line is a color-coded line where black represents the absence of any broken filaments or loops, the first color represents broken filaments, and the second color represents filament loops. An example of such a resultant map of broken filaments 130 and loops 131 is depicted in FIG. 23.

With respect to the foregoing description and drawing figures taken together as a whole, it will be readily appreciated that the present invention enables identification of abnormalities in yarn packages in a manner heretofore unknown in the art. With particular respect to overthrow detection, the present invention directly utilizes the inherent geometric relationship between the overthrows and the radial vectors of the yarn package on which they are wound. In doing so, the present invention is relieved from dependence upon unreliable measurement techniques currently practiced in the art. With particular respect to the detection of broken filaments and loops, the present invention advantageously utilizes an artificial horizon, and an evaluation of the pixels surrounding each suspected abnormality, for the purposes of properly and reliably detecting these abnormalities.

While the present invention has been generally described for use with yarn filaments, the present invention is equally applicable to synthetic and organic yarns, metal wiring, fiber optic cable or other line shaped materials which may alternatively be utilized without departing from the broader aspects of the present invention.

While the invention had been described with reference to the preferred embodiments, it will be understood by those skilled in the art that various obvious changes may be made, and equivalents may be substituted for elements thereof, without departing from the essential scope of the present invention. Therefore, it is intended that the invention not be limited to the particular embodiments disclosed, but that the invention includes all embodiments falling within the scope of the appended claims.

What is claimed is:

1. A filament inspection method for detecting abnormalities in a wound yarn package, said filament inspection method comprising the steps of:

illuminating said yarn package;

sensing and recording an image of said illuminated yarn package;

determining if a straight line segment exists in said recorded image; and evaluating said recorded image in accordance with predetermined criteria to determine thereby whether said recorded image indicates the presence of said abnormalities in said yarn package.

2. The filament inspection method according to claim 1, further comprising the steps of:

determining if said straight line segment is substantially perpendicular to a radial line of said yarn package; and identifying said straight line-segment as an overthrow abnormality when said straight line segment is substantially perpendicular to said radial line of said yarn package.

3. The filament inspection method according to claim 2, further comprising the steps of:

selecting a region of interest in said recorded image, said region of interest having an area smaller than said recorded image; and identifying said straight line segment as said overthrow abnormality when said straight line segment intersects a lower and an upper boundary of said region of interest.

4. The filament inspection method according to claim 2, further comprising the steps of:

optically sensing and recording said image; and rotating said yarn package during said optical sensing and recording.

5. The filament inspection method according to claim 4, further comprising the steps of:

optically sensing and recording a plurality of images as said yarn package is rotated.

6. The filament inspection method according to claim 5, further comprising the steps of:

optically sensing and recording a separate image of said illuminated yarn package for every degree of rotation; and rotating said yarn package 360°.

7. The filament inspection method according to claim 6, further comprising the steps of:

delineating a region of interest in each of said separate images, said region of interest having an area smaller than each of said separate images; and identifying said straight line segment as an abnormality when said straight line segment intersects a lower and an upper boundary of said region of interest.

8. The filament inspection method according to claim 2, further comprising the steps of:

selecting a region of interest in said recorded image, said region of interest having an area smaller than said recorded image; and converting said recorded image to a binary image.

9. The filament inspection method according to claim 8, further comprising the steps of:

designating a pixel in said binary image as an object pixel;

determining a greyscale value for a predetermined number of pixels on both sides of said object pixel;

marking said object pixel in said binary image as either a white pixel or a black pixel in dependence upon said evaluated greyscale values.

10. The filament inspection method according to claim 9, further comprising the steps of:

marking said object pixel as a black pixel in said binary image if a difference between said determined greyscale values for said predetermined number of pixels on both sides of said object pixel is below a predetermined greyscale value; and marking said object pixel as a white pixel in said binary image if said difference between said determined greyscale values for said predetermined number of pixels on both sides of said object pixel is equal to or greater than said predetermined greyscale value.

11. The filament inspection method according to claim 10, further comprising the steps of:

said predetermined number of pixels is proportional to a cross-sectional area of a strand of said yarn in said yarn package.

12. The filament inspection method according to claim 1, further comprising the steps of:

illuminating said yarn package with a bounded light pattern having sharply defined edges; and sensing and recording an image of said illuminated yarn package, wherein said recorded image includes a tangential view of an exterior portion of said yarn package.

13. The filament inspection method according to claim 12, wherein said sensing and recording step further includes:

positioning an optical recording device at an angle parallel to a tangential surface of said yarn package.

14. The filament inspection method according to claim 12, further comprising the steps of:

converting said recorded image to a binary image;

establishing an artificial horizon for said binary image; and determining if a strand of said yarn package extends beyond said artificial horizon.

15. The filament inspection method according to claim 14, wherein said establishing an artificial horizon step further includes:

obtaining a mean height for said exterior portion; and establishing a height said artificial horizon in said binary image to be equal to said mean height.

16. The filament inspection method according to claim 14, further comprising the steps of:

evaluating each column of pixels comprising said binary image, said evaluation beginning at a top pixel of each of said pixel columns; and detecting when a white pixel is discovered during said evaluation of each of said pixel columns.

17. The filament inspection method according to claim 16, further comprising the steps of:

examining pixels adjacent said white pixel in said binary image; and identifying said white pixel as a portion of one of a broken yarn strand, a overhanging yarn strand and a yarn loop if a pattern of said adjacent pixels conforms to one of a plurality of abnormality criteria.

18. In The filament inspection method according to claim 1, further comprising the steps of:

illuminating said yarn packages with a first illumination source outputting a light of a first color, and a second illumination source outputting a light of a second color;

wherein said first color is different from said second color.

19. A filament inspection apparatus for identifying abnormalities in wound yarn packages, said inspection apparatus comprising:

an illumination device for directing light onto said yarn package;

a recording device for sensing and recording an image of said illuminated yarn package;

a controller for delineating a region of interest within said image, said region of interest having an area smaller than an area of said image and being intersected by a radial line of said yarn package; and a determination device for determining if any straight image lines existing in said image are substantially perpendicular to said radial line.

20. The filament inspection apparatus according to claim 19, wherein:

said controller marks said straight image lines as an overthrow abnormality when said straight image line is substantially perpendicular to said radial line.

21. A filament inspection apparatus for identifying abnormalities in wound yarn packages, said inspection apparatus comprising:

an illumination device for illuminating said yarn package with a bounded light pattern having sharply defined edges;

a recording device for sensing and recording an image of said illuminated yarn package, wherein said recorded image includes a tangential view of an exterior portion of said yarn package; and a controller for converting said recorded image to a binary image and establishing an artificial horizon of said exterior portion, wherein said controller marks any strands of yarn extending beyond said artificial horizon as one of a broken filament abnormality, an overhanging filament abnormality and a filament loop abnormality.

22. A filament inspection method for detecting abnormalities in a wound yarn package, said filament inspection method comprising the steps of:

illuminating a portion of said yarn package;

sensing and recording an image of said illuminated portion of said yarn package, wherein said illuminated portion comprises a geometric shape having a non-uniform width; and evaluating said recorded image in accordance with predetermined criteria to determine thereby whether said recorded image indicates the presence of said abnormalities in said yarn package.

23. The filament inspection method according to claim 22, further comprising the steps of:

forming said geometric shape to be a trapezoidal shape defining a short side and a long side, said short side and said second side being parallel to one another;

orienting said short side adjacent a center of said yarn package; and orienting said long side adjacent an outer circumference of said yarn package.

* * * * *